(12) United States Patent
Bongers et al.

(10) Patent No.: US 11,109,764 B2
(45) Date of Patent: Sep. 7, 2021

(54) SINGLE HEAT FLUX SENSOR ARRANGEMENT

(71) Applicant: KONINKLIJKE PHILIPS N.V., Eindhoven (NL)

(72) Inventors: Edwin Gerardus Johannus Maria Bongers, Eindhoven (NL); Antonius Hermanus Maria Blom, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 327 days.

(21) Appl. No.: 16/300,108

(22) PCT Filed: May 18, 2017

(86) PCT No.: PCT/EP2017/062034
§ 371 (c)(1),
(2) Date: Nov. 9, 2018

(87) PCT Pub. No.: WO2017/198788
PCT Pub. Date: Nov. 23, 2017

(65) Prior Publication Data
US 2019/0142280 A1    May 16, 2019

(30) Foreign Application Priority Data

May 18, 2016  (EP) .................................. 16170086

(51) Int. Cl.
*A61B 5/01*    (2006.01)
*A61B 5/00*    (2006.01)
(Continued)

(52) U.S. Cl.
CPC .............. *A61B 5/01* (2013.01); *A61B 5/0002* (2013.01); *A61B 5/681* (2013.01); *A61B 5/6801* (2013.01);
(Continued)

(58) Field of Classification Search
CPC ...... G01K 1/165; G01K 13/002; G01K 13/00; G01K 17/00; G01K 17/20; G01K 5/24;
(Continued)

(56) References Cited

U.S. PATENT DOCUMENTS 9,113,774 B2   8/2015  Goto
9,164,000 B2  10/2015  Augustine
(Continued)

FOREIGN PATENT DOCUMENTS

CN   101568814 A  * 10/2009  ........... G01K 13/002
CN   102378905 A  *  3/2012  ............... A61B 5/01
(Continued)

OTHER PUBLICATIONS

Kitamura K, Zhu X, Chen W, Nemoto T. Development of a new method for the noninvasive measurement of deep body temperature without a heater. Med Eng Phys. Jan. 2010;32(1):1-6. doi: 10.1016/j.medengphy.2009.09.004. Epub Nov. 10, 2009. PMID: 19906554. (Year: 2009).*

(Continued)

*Primary Examiner* — Catherine B Kuhlman
*Assistant Examiner* — William A Anderson

(57) ABSTRACT

The invention describes a single heat flux sensor arrangement (1) comprising a sensor (10) comprising a layer (100) of thermally insulating material, an inner temperature measurement means (S1) arranged at an inner region of the insulating layer (100) and an outer temperature measurement means (S2) arranged at an outer region of the insulating layer (100); an evaluation unit (11) adapted to receive a temperature input from the inner 5 temperature measurement means (S1) and to receive a temperature input from the outer temperature measurement means (S2); and a heating means (12, S2) realized to deliberately raise the temperature of a region of the insulating layer (100). The invention (Continued)

further describes a non-invasive method of measuring a core body temperature (T0) of a subject (3).

20 Claims, 3 Drawing Sheets

(51) Int. Cl.
G01K 13/20 (2021.01)
G01K 1/16 (2006.01)
(52) U.S. Cl.
CPC ............ *A61B 5/6823* (2013.01); *A61B 5/742* (2013.01); *G01K 1/165* (2013.01); *G01K 13/20* (2021.01); *A61B 2562/0271* (2013.01)
(58) Field of Classification Search
CPC ............... G01K 13/20; A61B 5/02055; A61B 2018/00791; A61B 5/01–015; A61B 2562/0271; A61B 5/6801; A61B 5/0002; A61B 5/6831; A61B 5/0008; A61B 8/546
See application file for complete search history.

(56) References Cited

U.S. PATENT DOCUMENTS

| | | | |
|---|---|---|---|
| 2002/0191675 | A1 | 12/2002 | Tokita et al. |
| 2005/0043631 | A1* | 2/2005 | Fraden ..................... G01K 1/20 600/474 |
| 2006/0056487 | A1 | 3/2006 | Kuroda et al. |
| 2007/0106172 | A1* | 5/2007 | Abreu .................. A61B 5/0002 600/549 |
| 2011/0301493 | A1 | 12/2011 | Husheer |
| 2013/0331728 | A1* | 12/2013 | Sun ...................... G01K 13/002 600/549 |
| 2017/0100042 | A1* | 4/2017 | Shrubsole ................ A61B 5/01 |

FOREIGN PATENT DOCUMENTS

| | | |
|---|---|---|
| DE | 102006012338 B3 | 7/2007 |
| WO | 2008068665 A1 | 6/2008 |
| WO | 2008078271 A1 | 7/2008 |
| WO | 2010014354 A1 | 2/2010 |

OTHER PUBLICATIONS

Machine translation of Patent No. CN 101568814 A, retrieved from worldwide.espacenet.com, on Dec. 2, 2020 (Year: 2009).*
Machine translation of Patent No. CN 102378905 A, retrieved from worldwide.espacenet.com, on Dec. 15, 2020 (Year: 2012).*
V. L. Young, et al., "Prevention of perioperative hypothermia in plastic surgery," Aesthetic Surg. J. Am. Soc. Aesthetic Plast. Surg., vol. 26, No. 5, pp. 551-571, Oct. 2006.
P. S. Barie, "Surgical site infections: epidemiology and prevention," Surg. Infect., vol. 3, 2002, Suppl 1, pp. S9-21. (Abstract).
Gunga, et al., "A non-invasive device to continuously determine heat strain in humans", Journal of Thermal Biology, vol. 33, Issue 5, Jul. 2008, pp. 297-307. (Abstract).
Kitamura, et al., "Development of a new method for the noninvasive measurement of deep body temperature without a heater". Medical Engineering & Physics, vol. 32, Issue 1, Jan. 2010, pp. 1-6. (Abstract).
Sy, et al., "A nonintrusive temperature measuring system for estimating deep body temperature in bed", Engineering in Medicine and Biology Society (EMBS), 2012 Annual International Conference of the IEEE, Aug. 28, 2012, pp. 3460-3463.(Abstract).
Fox RH, et al., "A new method for monitoring deep body temperature from the skin surface", Clinical Science 1973;44:81-86.
http://www.ctherm.com/products/tci_thermal_conductivity/helpful_links_tools/thermal_resistance_thermal_conductance/ (Abstract).

* cited by examiner

SINGLE HEAT FLUX SENSOR ARRANGEMENT

This application is the U.S. National Phase application under 35 U.S.C. § 371 of International Application No. PCT/EP2017/062034, filed on May 18, 2017, which claims the benefit of European Application Serial No. 16170086.9, filed May 18, 2016. These applications are hereby incorporated by reference herein.

FIELD OF THE INVENTION

Embodiments of the invention describe a single heat flux sensor arrangement and a method of measuring a core body temperature of a subject.

BACKGROUND OF THE INVENTION

In a healthcare environment, it is often necessary to accurately monitor the core body temperature of a patient. The core body temperature may be understood to be the temperature of blood through the vital organs such as the heart and brain. Its measurement is of great importance in hospital care. This is especially evident for patients undergoing long surgical procedures in cooled operating rooms, since a patient under anesthetic cannot regulate his or her body temperature. This can be a serious problem, and it is estimated that up to 50% of all surgical patients suffer from hypothermia following a surgical procedure.

One way of monitoring the core body temperature is to use an invasive probe, for example an esophageal probe, a rectal probe, etc. Since the core body temperature must be monitored over an extended period of time, such probes are generally perceived as very uncomfortable by the conscious patient. A non-invasive temperature monitoring device can be based on the concept of zero heat flux. However, such a sensor requires a control loop and heating elements to actively achieve "zero heat flow", making this kind of sensor difficult to integrate in a wearable sensor application.

Measurement of core body temperature is also possible using passive sensing. There are two main approaches in performing passive core body temperature measurement. One approach requires only two temperature measuring devices separated by an insulating material. It is assumed that the thermal resistivity of the insulating materials is known, while the skin thermal resistivity is estimated, usually taking an average value that is assumed to apply to any patient of any age. Once an equilibrium is reached (the temperature reported by a temperature measuring device has reached a constant level) the heat flow between the two temperature measuring devices can be calculated, and the core body temperature is then determined. The advantages of a passive "single heat flux sensor" are its simple geometry, a thin realization, straightforward calculations, and the fact that only two temperature measuring devices are needed. However, even disregarding the slight inaccuracy owing to the fact that heat flow is not limited to the outward direction only, a more serious inaccuracy can arise from assuming a value for the skin thermal resistivity. A patient may have a skin thermal resistivity that is not the same as the average value, so that the core body temperature for that patient will not be reported correctly. Furthermore, the skin thermal resistivity can vary even for one patient, and can be different at the forehead, arm, chest, etc.

An alternative passive approach measures two heat flows. In such a "dual heat flux sensor", the sensor pad has two layers of different thickness, and at least four temperature measuring devices. The sensor can estimate core body temperature without making any assumptions regarding the skin thermal resistivity. The advantage of a passive dual heat flux sensor is that it delivers a more accurate temperature reading. However, a dual heat flux sensor has a more complex geometry and is more expensive to manufacture; is significantly more bulky; needs at least four temperature measuring devices; requires complex calculations to be performed; has a long heating time to reach equilibrium; and is prone to error.

Therefore, it is an object of the invention to provide an improved single heat flux sensor for measuring the core temperature of a subject.

SUMMARY OF THE INVENTION

The object of the invention is achieved by a single heat flux sensor arrangement, and by a method of measuring a core body temperature of a subject.

According to embodiments of the invention, the single heat flux sensor arrangement comprising a sensor comprising a layer of thermally insulating material, an inner temperature measurement means arranged at an inner region of the insulating layer and an outer temperature measurement means arranged at an outer region of the insulating layer; an evaluation unit adapted to receive a temperature input from the inner temperature measurement means and to receive a temperature input from the outer temperature measurement means; and a heating means realized to deliberately raise the temperature of a region of the insulating layer, for example to raise the temperature of one of the thermistors. The evaluation unit can then calculate a value of thermal resistivity for the subject, and can use this information to accurately determine the core body temperature of the subject.

An advantage of the inventive single heat flux sensor arrangement is that it combines the advantages of a single heat flux sensor and a dual heat flux sensor, i.e. it has the simple construction of a single heat flux sensor but achieves the better measurement accuracy of a dual heat flux sensor. By also comprising the heating means to deliberately raise the temperate of the sensor, it is possible, as will be explained below, to determine the thermal resistivity of the subject. Because this thermal resistivity is calculated instead of simply being estimated—as in the conventional approach—the accuracy of the temperature measurement can be significantly improved. The manufacturing costs of the inventive sensor compare favorably to conventional single heat flow sensors, and are significantly lower than dual heat flow sensors.

According to the embodiments, the non-invasive method of measuring a core body temperature of a subject comprises the steps of attaching such a single heat flux sensor arrangement to a subject; determining a first equilibrium temperature and subsequently activating the heating means to heat the outer region of the insulating layer of the sensor; determining a second equilibrium temperature; determining a value of thermal resistivity for that subject; and calculating the core body temperature of the subject on the basis of the thermal resistivity value and an equilibrium temperature.

The inventive method allows a more precise computation of the subject's core temperature, since it also includes a step of determining the thermal resistivity for that subject. This compares favorably with conventional single heat flux temperature sensing methods that rely on an estimated thermal resistivity value for the subject.

The dependent claims and the following description discloses particularly advantageous embodiments and features. Features of the embodiments may be combined as appropriate. Features described in the context of one claim category can apply equally to another claim category.

The terms "heat flux" and "heat flow" are understood to be synonymous, and are used interchangeably in the following. The inventive single heat flux sensor arrangement can be used to measure the temperature of any subject for which it is not practicable to determine the subject's thermal resistivity. In the following, but without restricting the embodiments in any way, it may be assumed that the subject is a human patient, and that the temperature to be observed is the patient's core body temperature.

A temperature measurement means can comprise any suitable type of temperature sensor. Thermistors are often used in small-scale devices to measure temperature on account of their favorably small size, their sensitivity, accuracy and the ability to easily incorporate them into an electrical circuit. Therefore, it may be assumed in the following that a temperature measurement means is a thermistor.

The thermally insulating layer or sensor pad can comprise any suitable material such as polymer foam. It may be assumed that a value of the thermal resistivity of the material can be obtained from the manufacturer of the thermally insulating material. Alternatively it is relatively straightforward to determine this value, as will be known to the skilled person.

The evaluation unit preferably comprises a suitable interface that allows it to receive a signal from each thermistor. For example, a thermistor can be connected in the overall circuit to deliver a voltage signal that is indicative of the temperature at the location of the thermistor. When the sensor is placed on the patient's skin, the temperature of the thermistors will alter in response to the heat flow through the sensor pad. To interpret the incoming information, the evaluation unit preferably comprises a suitable processing unit. The processing unit can be a microprocessor with a number of suitable interfaces, and can be realized to perform any necessary computations in order to determine an equilibrium temperature condition of the sensor. Such an equilibrium condition is attained when each thermistor reports a stable value over time.

For example, the processing unit can continuously compare the thermistor input signals, and when each of these has remained essentially constant or unchanging for an appropriate length of time (e.g. a few seconds), the processing unit can assume that a first equilibrium temperature has been reached. At this point, the processing unit can record a first temperature value for the inner thermistor and a first temperature value for the outer thermistor, and then subsequently activates the heating means.

The heating means could be realized as a wire loop embedded in the sensor pad. This could be heated from an external source, for example by passing a current through the wire. Instead of a resistive wire loop, one or more resistors can be implemented in the sensor pad to achieve the desired heating function. In an embodiment of the invention, the outer thermistor itself is used to raise the temperature of the sensor at the outer region, using the fact that a thermistor is essentially a resistive component. This advantageous realization eliminates the need for a separate heating element. In the embodiment of the invention, a current is passed through the thermistor to raise its temperature. To this end, the heating means of the inventive single heat flux sensor arrangement comprises a current source.

The evaluation unit is preferably realized to activate the heating means in response to a first equilibrium temperature condition of the sensor, for example by issuing a trigger signal to the current source. As long as the heating means is active, the processing unit continues to compare the thermistor input signals, and when these have been essentially equal for an appropriate length of time (e.g. a few seconds), the processing unit can assume that a second thermal equilibrium condition has been reached. At this point, the processing unit can record a second temperature value for the inner thermistor and a second temperature value for the outer thermistor.

With the information collected by the evaluation unit, namely the first and second temperature values for each thermistor, and the known thermal resistivity value of the sensor pad insulating material, it is possible to calculate the skin thermal resistivity. This then allows the evaluation unit to calculate a more precise core body temperature during the subsequent temperature monitoring procedure. The method stages and the relevant mathematical equations will be explained in more detail with the aid of the diagrams.

After the second equilibrium condition has been determined, the heating means can be turned off. Alternatively, in a further embodiment of the invention, the heating source is not switched off after reaching the second thermal equilibrium but remains turned on. In this embodiment, the level of heating is chosen to essentially minimize the thermal flux through the sensor pad. The resulting state resembles that of zero heat flux. In that state, the fraction that must be added to (or subtracted from) the temperature measured by the first thermistor to obtain the core temperature becomes small. The error associated with that fraction also becomes small.

Preferably, the inventive sensor arrangement is equipped with a suitable memory module that can record a temperature profile for the core body temperature of the patient. This can be displayed as visual feedback in a display unit, for example. In a further embodiment of the invention, the sensor arrangement is realized as a wearable device, for example to be worn as a cuff on the patient's arm, or to be attached by an adhesive patch to the patient's chest, etc. The display unit could be an integral part of the wearable device. Alternatively or in addition, the sensor arrangement might be equipped with a wireless interface that can transmit core body temperate values, or an entire temperature profile, at intervals to a remote monitoring station.

The single flux sensor arrangement according to the embodiments can be in place on a patient throughout a perioperative period, as well as during transport of a patient to and from the operating room. It may also be useful for monitoring patients in a general hospital ward or in an intensive care unit.

Other objects and features of the present embodiments will become apparent from the following detailed descriptions considered in conjunction with the accompanying drawings. It is to be understood, however, that the drawings are designed solely for the purposes of illustration and not as a definition of the limits of the invention.

BRIEF DESCRIPTION OF THE DRAWINGS

In the drawings, like numbers refer to like objects throughout. Objects in the diagrams are not necessarily drawn to scale.

DETAILED DESCRIPTION OF THE EMBODIMENTS

Figure 1:
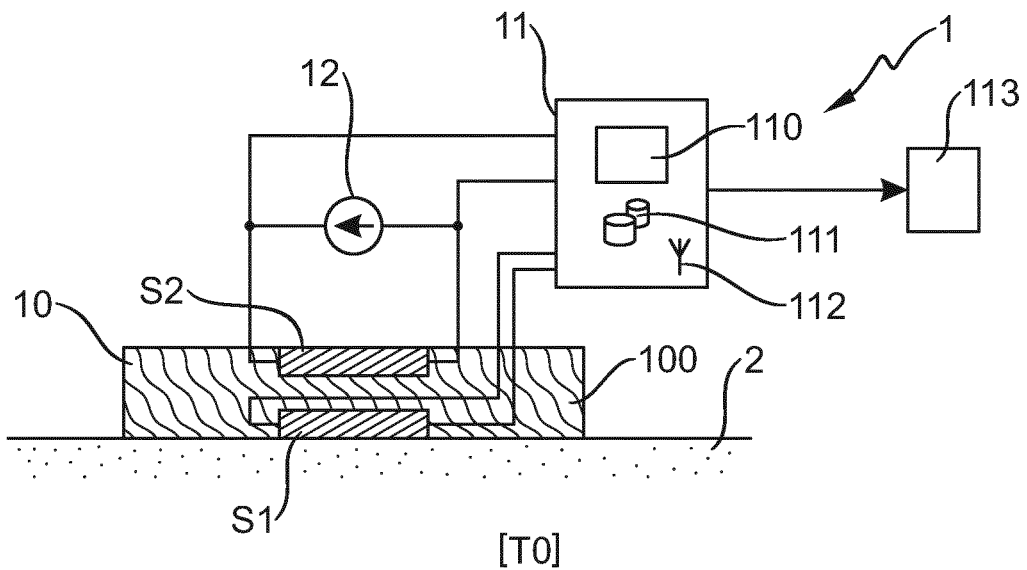
FIG. 1 shows a block diagram of the single heat flow sensor according to a representative embodiment.

FIG. 1 shows an exemplary embodiment of the inventive single heat flux sensor arrangement 1. The heat flux sensor arrangement 1 comprises a sensor 10, which mainly consists of a thermally insulating layer 100 or pad 100. The sensor 10 is applied to the skin 2 of a patient, and the heat flux sensor arrangement 1 will be used to determine the patient's core body temperature.

The sensor 10 has an inner thermistor S1 arranged at or close to an inner surface of the pad 100, and an outer thermistor S2 arranged at or close to an outer surface of the pad 100. An evaluation unit 11 is electrically connected to the thermistors and can evaluate the electrical signals that it receives in order to determine a temperature T1 at the inner region of the pad 100 and a temperature T2 at the outer region of the pad 100. To this end, the evaluation unit 11 can comprise a suitable microprocessor, FPGA, etc.

In this exemplary embodiment, the single heat flow sensor 1 has a memory module 111 for recording a temperature profile, and is also equipped with a transmitter 112 for sending a temperature profile and/or recorded temperature measurements to a remote monitoring station. The diagram also indicates that the single heat flux sensor arrangement 1 can be connected to or equipped with a display unit 113 (for example in the manner of a smart watch) for showing a temperature profile to a user, for example the patient or a caregiver.

The inventive heat flux sensor arrangement 1 has a heating means 12 realized to raise the temperature of the outer thermistor S2. In this exemplary embodiment, the heating means 12 is a current source, and is controlled by the evaluation unit 11 to apply a current through the outer thermistor S2 for a predefined duration. This allows additional information to be collected, so that the thermal resistivity of the skin 2 can be determined, as will be explained in the following.

Figure 2:
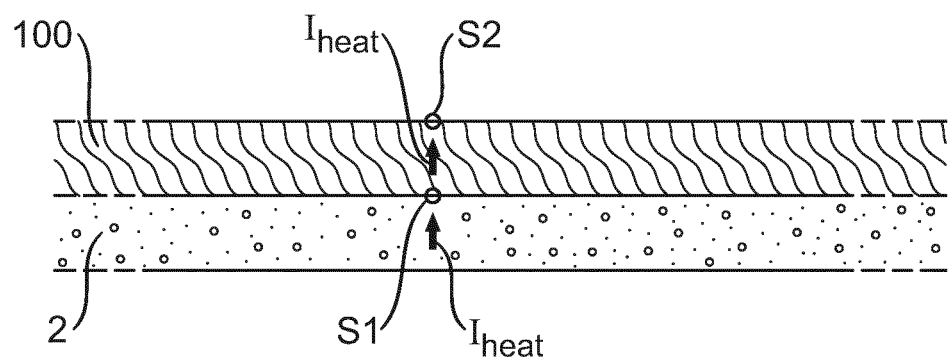
FIG. 2 shows a simplified diagram of an ideal single heat flux sensor.

FIG. 2 illustrates the principle of operation of a single heat flux sensor applied to the skin 2 of a person. This relatively simple sensor construction uses only two temperature sensors S1, S2 separated by the layer of thermally insulating material of the pad 100. The heat flow $I_{heat}$ through the skin 2 and through the sensor pad 100 will be the same, and can be expressed as $$I_{heat} = \frac{T1 - T2}{R1} = \frac{T0 - T1}{R0} \quad (1)$$

where T1 is the temperature at the inner sensor S1, T2 is the temperature at the outer sensor S2, R1 is the thermal resistivity of the thermally insulating material of the pad 100, and R0 is the skin thermal resistivity. The thermal resistivity R1 of the insulating material may be presumed to be known. An expression for the core body temperature T0 can be obtained by re-arranging equation (1):

$$T0 = T1 + \frac{(T1 - T2)R0}{R1} \quad (2)$$

Equations (1) and (2) are based on the presumption that the material layers of the skin 2 and the pad 100 are infinitely wide, so that the heat can be presumed to flow only in the vertical direction, as indicated by the arrows. In a practical application, there will also be a lateral heat flow component which will detract from the accuracy of the measurement results. Furthermore, only the thermal resistivity R1 of the sensor pad is known, and the skin thermal resistivity R0 must be estimated. This can significantly detract from the accuracy of the measurement results, since the skin thermal resistivity can vary depending on which part of the body the sensor is attached to, and values of skin thermal resistivity can vary significantly between people depending on various factors such as age, physiology, etc.

Figure 3A:
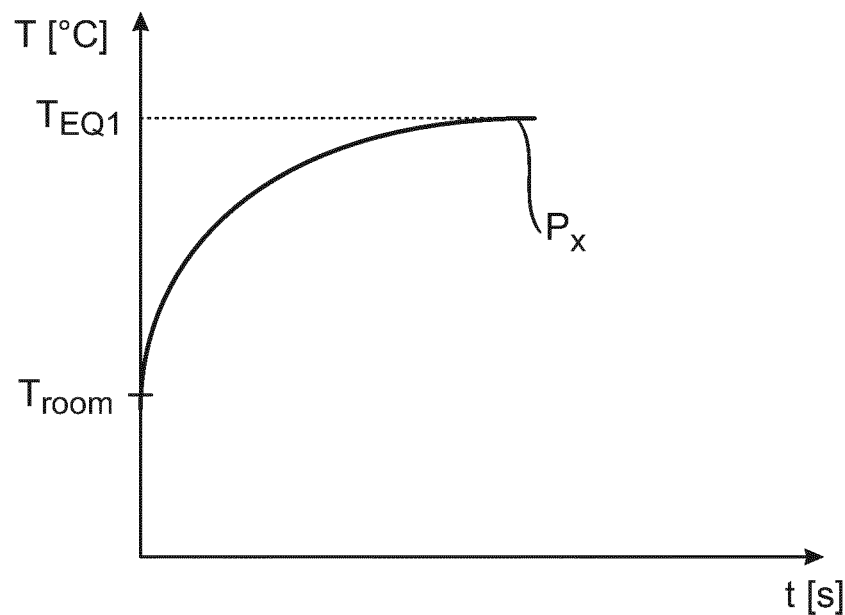
FIG. 3A illustrates a first stage in the method according to a representative embodiment.
Figure 3B:
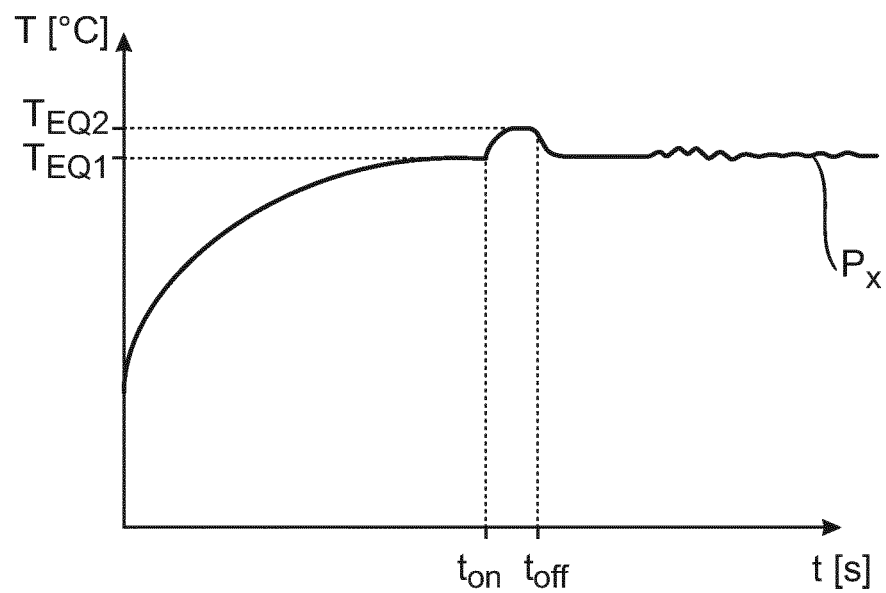
FIG. 3B illustrates a second stage in the method according to a representative embodiment.

The inventive sensor can overcome this limitation of the conventional sensors by actually measuring the skin thermal resistivity. FIGS. 3A and 3B will be used to explain the stages of the method. Initially a thermistor of the sensor 10 may be assumed to have ambient or room temperature $T_{room}$. After attaching the sensor 10 to the skin 2, heat flow from the patient's body will raise the temperature of the sensor pad 100, so that the thermistors also report rising temperatures. A temperature profile $P_x$ for one of the thermistors in the first stage of the method is shown in FIG. 3A. Ultimately, the temperature of the thermistor will reach an equilibrium temperature $T_{EQ1}$. At this point, using equation (2) above, the core body temperature can be expressed as $$T0 = T11 + \frac{(T11 - T21)R0}{R1} \quad (3)$$

where T11 is the initial inner thermistor temperature value and T21 is the initial outer thermistor temperature value. As explained above, R1 is a known quantity, and T11, T21 are measured values. The remaining unknowns are the skin thermal resistivity R0 and the core body temperature T0.

In the second stage, the outer thermistor S2 is heated for a brief duration by turning on the heating means 12 at time $t_{on}$ to apply a current through this outer thermistor S2. The heating arrangement can be controlled such that the temperature at the outer thermistor S2 is only slightly raised, i.e. so that it will not be raised above core body temperature level. A new equilibrium temperature TEQ2 is reached after a while, as illustrated in FIG. 3B. The thermistor temperatures are recorded and current is switched off at time $t_{off}$. Again, using equation (2) above, the core body temperature can be expressed as $$T0 = T12 + \frac{(T12 - T22)R0}{R1} \quad (4)$$

where T12 is the second inner thermistor temperature value and T22 is the second outer thermistor temperature value. In this case also, R1 is a known quantity, T12, T22 are measured values, and the remaining unknowns are the skin resistivity R0 and the core body temperature T0. By reversing the thermal flux, T22 will be higher than T12, so that equation (4) describes a core temperature value that is lower than T12.

The inventive method allows the skin thermal resistivity R0 to be expressed in terms of the measured quantities, by equating equations (3) and (4) above and solving for skin thermal resistivity R0 to give:

$$R0 = \frac{T12 - T11}{T11 - T21 + T22 - T12} \cdot R1 \quad (5)$$

Instead of assuming that the patient's skin resistivity is the same as an average value, the patient's skin resistivity R0 has been measured to a satisfactory degree of accuracy and is now patient-specific as well as location-specific. This allows equation (2) to be used throughout the temperature monitoring procedure to accurately report the patient's core body temperature. In this way, the core body temperature of the patient can be accurately estimated in an entirely non-invasive manner.

Figure 4:
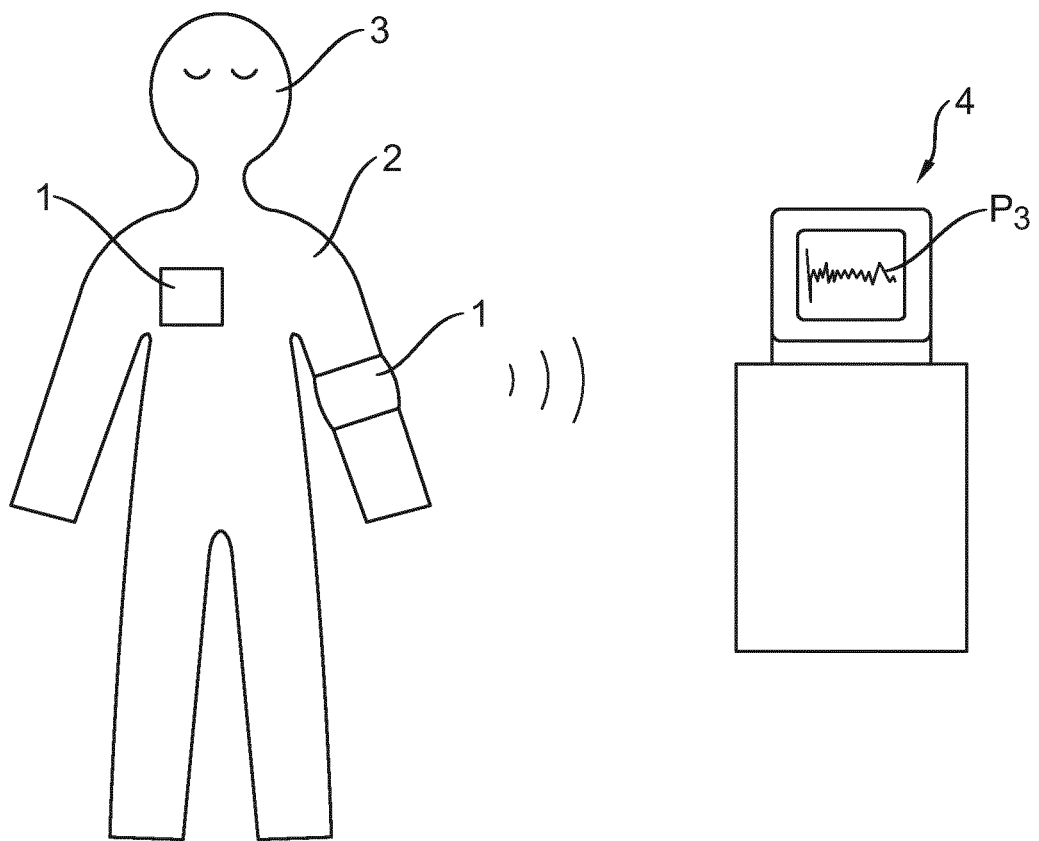
FIG. 4 shows an embodiment of the single heat flow sensor according to a representative embodiment.

FIG. 4 shows the inventive single heat flux sensor arrangement 1 realized as a wearable device, and indicates two of several possible locations, namely on the chest or around the arm. In each case, the sensor pad has been attached to the skin 2 of a patient 3. A visual readout of the patient's core body temperature T0, as computed using the method explained above, can be shown as a temperature profile $P_3$. The wearable device might include a small display so that the patient or caregiver can observe the core body temperature development. Alternatively, the wearable device can send the information to a remote monitoring station 4 where the temperature profile $P_3$ may be shown on a display.

Although the present invention has been disclosed in the form of representative embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A heat flux sensor arrangement for measuring a core body temperature of a subject, comprising:
    a sensor comprising a thermally insulating layer of thermally insulating material, an inner temperature sensor arranged at an inner region of the thermally insulating layer, and an outer temperature sensor arranged at an outer region of the thermally insulating layer;
    a heater configured to raise a temperature in the thermally insulating layer; and
    a processing unit configured to receive a temperature input from the inner temperature sensor, to receive a temperature input from the outer temperature sensor, to calculate a value of thermal resistivity R0 of the subject according to $$R0 = \frac{T12 - T11}{T11 - T21 + T22 - T12} \cdot R1$$

wherein T11 is a first inner temperature sensor temperature value, T12 is a second inner temperature sensor temperature value, T21 is a first outer temperature sensor temperature value, T22 is a second outer temperature sensor temperature value, and R1 is thermal resistivity of the thermally insulating layer, and
    to calculate the core body temperature of the subject based on the calculated thermal resistivity R0 of the subject.

2. The heat flux sensor arrangement according to claim 1, wherein the processing unit is further configured to determine an equilibrium temperature condition of the sensor, wherein the equilibrium temperature condition is attained when each of the inner temperature sensor and the outer temperature sensor reports a stable value over time.

3. The heat flux sensor arrangement according to claim 2, wherein the processing unit is further configured to activate the heater in response to a first equilibrium temperature condition of the sensor.

4. The heat flux sensor arrangement according to claim 3, wherein the processing unit is further configured to deactivate the heater in response to a second equilibrium temperature condition of the sensor.

5. The heat flux sensor arrangement according to claim 1, wherein the heater is configured to raise the temperature of the thermally insulating layer at the outer region of the thermally insulating layer.

6. The heat flux sensor arrangement according to claim 1, wherein the inner temperature sensor comprises an inner thermistor and the outer temperature sensor comprises an outer thermistor.

7. The heat flux sensor arrangement according to claim 6, wherein the heater is configured to apply an electric current through the outer thermistor.

8. The heat flux sensor arrangement according to claim 1, wherein the heater comprises a current source.

9. The heat flux sensor arrangement according to claim 1, further comprising a memory configured to record temperature-related data collected by the sensor.

10. The heat flux sensor arrangement according to claim 1, wherein the heat flux sensor arrangement is a wearable device.

11. The heat flux sensor arrangement according claim 1, further comprising a display configured to display a temperature profile of the core body temperature of the subject.

12. The heat flux sensor arrangement according to claim 1, further comprising a wireless interface for communication with a remote monitoring station.

13. A method of measuring a core body temperature of a subject, comprising:
    attaching a sensor to the subject, the sensor comprising a heater, a thermally insulating layer of thermally insulating material, an inner temperature sensor arranged at an inner region of the thermally insulating layer, and an outer temperature sensor arranged at an outer region of the thermally insulating layer;
    determining a first equilibrium temperature of one of the inner temperature sensor or the outer temperature sensor, and subsequently activating the heater to heat the outer region of the thermally insulating layer of the sensor;
    determining a second equilibrium temperature of the one of the inner temperature sensor or the outer temperature sensor;
    subsequently calculating a value of thermal resistivity R0 of the subject according to $$R0 = \frac{T12 - T11}{T11 - T21 + T22 - T12} \cdot R1$$

wherein T11 is a first inner temperature sensor temperature value, T12 is a second inner temperature sensor temperature value, T21 is a first outer temperature sensor temperature value, T22 is a second outer temperature sensor temperature value, and R1 is thermal resistivity of the thermally insulating layer; and calculating the core body temperature of the subject based on the calculated thermal resistivity value.

14. The method according to claim 13, further comprising a de-activating the heater after determining the second equilibrium temperature.

15. The method according to claim 13, further comprising deactivating the heater in response to attaining the second equilibrium temperature.

16. The method according to claim 13, wherein the inner temperature sensor comprises an inner thermistor and the outer temperature sensor comprises an outer thermistor, and wherein the outer region of the thermally insulating layer of the sensor is heated by applying an electric current through the outer thermistor.

17. A heat flux sensor device comprising:

a sensor configured to contact skin of a subject, the sensor comprising an thermally insulating layer, an inner thermistor at an inner region of the thermally insulating layer to be arranged adjacent to the skin, and an outer thermistor at an outer region of the thermally insulating layer, wherein the thermally insulating layer has a thermal resistivity R1;

a heater configured to heat at least the outer region of the thermally insulating layer, and a processing unit programmed to:
receive a first inner temperature value T11 from the inner thermistor at a first equilibrium temperature of the sensor,
receive a first outer temperature value T21 from the outer thermistor at the first equilibrium temperature of the sensor,
receive a second inner temperature value T12 from the inner thermistor at a second equilibrium temperature of the sensor higher than the first equilibrium temperature;
receive a second outer temperature value T22 from the outer thermistor at the second equilibrium temperature of the sensor; and
calculate a thermal resistivity value R0 of the subject according to:

$$R0 = \frac{T12 - T11}{T11 - T21 + T22 - T12} \cdot R1.$$

18. The heat flux sensor device of claim 17, wherein the processing unit is further programmed to calculate a core body temperature of the subject based on the calculated thermal resistivity value R0 of the subject.

19. The heat flux sensor device of claim 17, wherein the heater comprises an adjustable current source.

20. The heat flux sensor device of claim 17, further comprising a wireless interface enabling communication with a remote monitoring station.

* * * * *